US012667855B2

(12) United States Patent
Ishigami et al.

(10) Patent No.: US 12,667,855 B2
(45) Date of Patent: Jun. 30, 2026

(54) DISCHARGE DEVICE

(71) Applicant: Panasonic Intellectual Property Management Co., Ltd., Osaka (JP)

(72) Inventors: Yohei Ishigami, Osaka (JP); Makoto Imai, Shiga (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 419 days.

(21) Appl. No.: 18/250,173

(22) PCT Filed: Nov. 19, 2021

(86) PCT No.: PCT/JP2021/042676
§ 371 (c)(1),
(2) Date: Apr. 21, 2023

(87) PCT Pub. No.: WO2022/118685
PCT Pub. Date: Jun. 9, 2022

(65) Prior Publication Data
US 2023/0390792 A1 Dec. 7, 2023

(30) Foreign Application Priority Data

Dec. 4, 2020 (JP) ................................. 2020-202307

(51) Int. Cl.
*B05B 5/057* (2006.01)
*A61L 9/14* (2006.01)
(Continued)

(52) U.S. Cl.
CPC ................ *B05B 5/057* (2013.01); *A61L 9/14* (2013.01); *B05B 5/035* (2013.01); *B05B 5/0533* (2013.01)

(58) Field of Classification Search
CPC ......... A61L 9/14; B05B 5/057; B05B 5/0255; B05B 5/02533; B05B 5/035; B05B 5/033; H01T 19/04
See application file for complete search history.

(56) References Cited

U.S. PATENT DOCUMENTS 5,957,395 A * 9/1999 Howe ..................... B05B 5/053
239/691
2009/0001200 A1 1/2009 Mahori et al.
(Continued)

FOREIGN PATENT DOCUMENTS

CN 111052524 A 4/2020
JP 2006-000826 A 1/2006
(Continued)

OTHER PUBLICATIONS

International Search Report issued on Dec. 21, 2021 in International Patent Application No. PCT/JP2021/042676, with English translation.

(Continued)

*Primary Examiner* — Christopher R Dandridge
(74) *Attorney, Agent, or Firm* — Rimon P.C.

(57) ABSTRACT

Discharge device includes discharge electrode, voltage application circuit, and current limiting element. Discharge electrode is disposed to face counter electrode, and retains liquid. Voltage application circuit is electrically connected to discharge electrode and counter electrode with discharge electrode as a ground side. Voltage application circuit generates discharge between discharge electrode and counter electrode by applying a voltage between discharge electrode and counter electrode. Current limiting element is electrically connected to a side of discharge electrode opposite to counter electrode. Current limiting element limits a current flowing to discharge electrode.

12 Claims, 5 Drawing Sheets

(51) Int. Cl.
    *B05B 5/035*      (2006.01)
    *B05B 5/053*      (2006.01)

(56)          References Cited

U.S. PATENT DOCUMENTS

| | | |
|---|---|---|
| 2018/0029053 A1 | 2/2018 | Aono et al. |
| 2018/0034248 A1 | 2/2018 | Ishigami et al. |
| 2020/0269263 A1 | 8/2020 | Kikuchi et al. |
| 2020/0353488 A1 | 11/2020 | Ishigami et al. |
| 2021/0268524 A1 | 9/2021 | Ishigami et al. |

FOREIGN PATENT DOCUMENTS

| | | | | |
|---|---|---|---|---|
| JP | 2007-313460 A | | 12/2007 | |
| JP | WO2015/059853 | * | 4/2015 | ........... B05B 5/0536 |
| JP | 2018-020269 A | | 2/2018 | |
| JP | 2018-022574 A | | 2/2018 | |
| JP | 2019046635 | * | 3/2019 | .............. A61L 9/14 |
| JP | 2020-138109 A | | 9/2020 | |
| TW | 202013843 A | | 4/2020 | |
| TW | 202019040 A | | 5/2020 | |

OTHER PUBLICATIONS

The EPC Office Action dated Apr. 29, 2024 for the related European Patent Application No. 21900440.5.
English Translation of Chinese Search Report dated Apr. 27, 2025 for the related Chinese Patent Application No. 202180078540.X.
English Translation of Taiwan Search Report dated Sep. 26, 2025 for the related Taiwan Patent Application No. 110142267.

* cited by examiner

DISCHARGE DEVICE

CROSS-REFERENCE OF RELATED APPLICATIONS

This application is the U.S. National Phase under 35 U.S.C. § 371 of International Patent Application No. PCT/JP2021/042676, filed on Nov. 19, 2021, which in turn claims the benefit of Japanese Patent Application No. 2020-202307, filed on Dec. 4, 2020, the entire disclosures of which Applications are incorporated by reference herein.

TECHNICAL FIELD

The present disclosure relates generally to a discharge device, and more particularly to a discharge device including a discharge electrode.

BACKGROUND ART

PTL 1 describes an electrostatic atomization device (discharge device) that generates fine particles of water containing radicals (charged fine particle water). The electrostatic atomization device described in PTL 1 includes a discharge electrode, a counter electrode, and a Peltier unit (liquid supply unit). The counter electrode is positioned to face the discharge electrode. The Peltier unit supplies water to the discharge electrode.

In the electrostatic atomizing device described in PTL 1, a high voltage is applied between the discharge electrode and the counter electrode to generate discharge, and thus, water supplied to the discharge electrode is atomized to generate charged fine particle water containing radicals.

CITATION LIST

Patent Literature

PTL 1: Unexamined Japanese Patent Publication No. 2006-000826

SUMMARY OF THE INVENTION

In the field of the electrostatic atomization device described in PTL 1, radical generation efficiency is desirably improved.

An object of the present disclosure is to provide a discharge device capable of improving radical generation efficiency.

A discharge device according to one aspect of the present disclosure includes a discharge electrode, a voltage application circuit, and a current limiting element. The discharge electrode is disposed to face the counter electrode, and retains a liquid. The voltage application circuit is electrically connected to the discharge electrode and the counter electrode with the discharge electrode as a ground side. The voltage application circuit generates discharge between the discharge electrode and the counter electrode by applying a voltage between the discharge electrode and the counter electrode. The current limiting element is electrically connected to a side of the discharge electrode opposite to the counter electrode side. The current limiting element limits a current flowing through the discharge electrode.

In accordance with the discharge device according to one aspect of the present disclosure, it is possible to improve radical generation efficiency.

DESCRIPTION OF EMBODIMENT

Exemplary Embodiment

Figure 1:
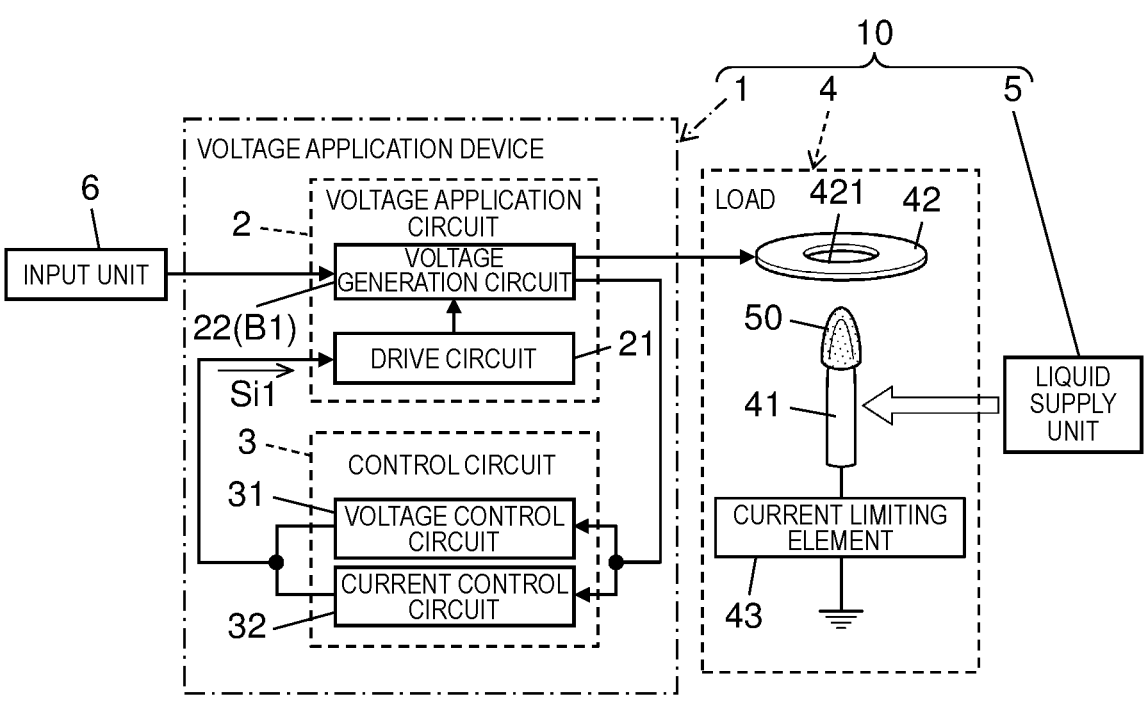
FIG. 1 is a block diagram illustrating a discharge device according to an exemplary embodiment.

Hereinafter, discharge device 10 according to an exemplary embodiment will be described with reference to FIGS. 1 to 8.

However, an exemplary embodiment and modifications to be described below are merely examples of the present disclosure, and the present disclosure is not limited to the exemplary embodiment and modifications. Even in a case other than the following exemplary embodiment and modifications, various modifications can be made in accordance with the design and the like without departing from the technical idea of the present disclosure.

Furthermore, all drawings to be described in the following exemplary embodiment are schematic diagrams, and ratios between sizes and thicknesses of components in the drawings do not necessarily reflect actual dimensional ratios.

(1) OUTLINE

First, an outline of discharge device 10 according to the present exemplary embodiment will be described with reference to FIG. 1. FIG. 1 is a block diagram of discharge device 10 according to the present exemplary embodiment.

As illustrated in FIG. 1, discharge device 10 according to the present exemplary embodiment includes voltage application device 1, load 4, and liquid supply unit 5. Voltage application device 1 is a device that applies a voltage for generating discharge to load 4, and includes voltage application circuit 2 and control circuit 3. Load 4 includes discharge electrode 41 and counter electrode 42. That is, discharge device 10 includes discharge electrode 41 and voltage application circuit 2. Furthermore, discharge device 10 further includes counter electrode 42. Counter electrode 42 is an electrode disposed to face discharge electrode 41 with a gap interposed therebetween. That is, discharge electrode 41 is disposed to face counter electrode 42. Load 4 generates discharge between discharge electrode 41 and counter electrode 42 by applying a voltage between discharge electrode 41 and counter electrode 42. Liquid supply unit 5 has a function of supplying liquid 50 to discharge electrode 41. As described above, discharge device 10 according to the present exemplary embodiment includes, as components, voltage application circuit 2, control circuit 3, liquid supply unit 5, discharge electrode 41, and counter electrode 42. However, discharge device 10 may include, as minimum components, voltage application device 1 and discharge electrode 41, and each of counter electrode 42 and liquid supply unit 5 may not be included in the components of discharge device 10.

For example, discharge device 10 according to the present exemplary embodiment applies a voltage from voltage application circuit 2 between discharge electrode 41 and counter electrode 42 in a state where liquid 50 adheres to a surface of discharge electrode 41 and liquid 50 is retained in discharge electrode 41. Accordingly, when discharge is generated between discharge electrode 41 and counter electrode 42, liquid 50 retained in discharge electrode 41 is electrostatically atomized by the discharge. That is, discharge device 10 according to the present exemplary embodiment constitutes a so-called electrostatic atomization device. In other words, discharge device 10 electrostatically atomizes liquid 50 retained in discharge electrode 41 by discharge generated between discharge electrode 41 and counter electrode 42. In the present disclosure, liquid 50 retained in discharge electrode 41, that is, liquid 50 to be electrostatically atomized is also simply referred to as "liquid 50".

Voltage application circuit 2 is electrically connected to discharge electrode 41 and counter electrode 42. Specifically, counter electrode 42 is electrically connected to a positive electrode (plus) of voltage application circuit 2, and discharge electrode 41 is electrically connected to a negative electrode (ground) of voltage application circuit 2. Voltage application circuit 2 applies a voltage between discharge electrode 41 and counter electrode 42. Accordingly, in load 4, discharge is generated between discharge electrode 41 and counter electrode 42.

Figure 4:
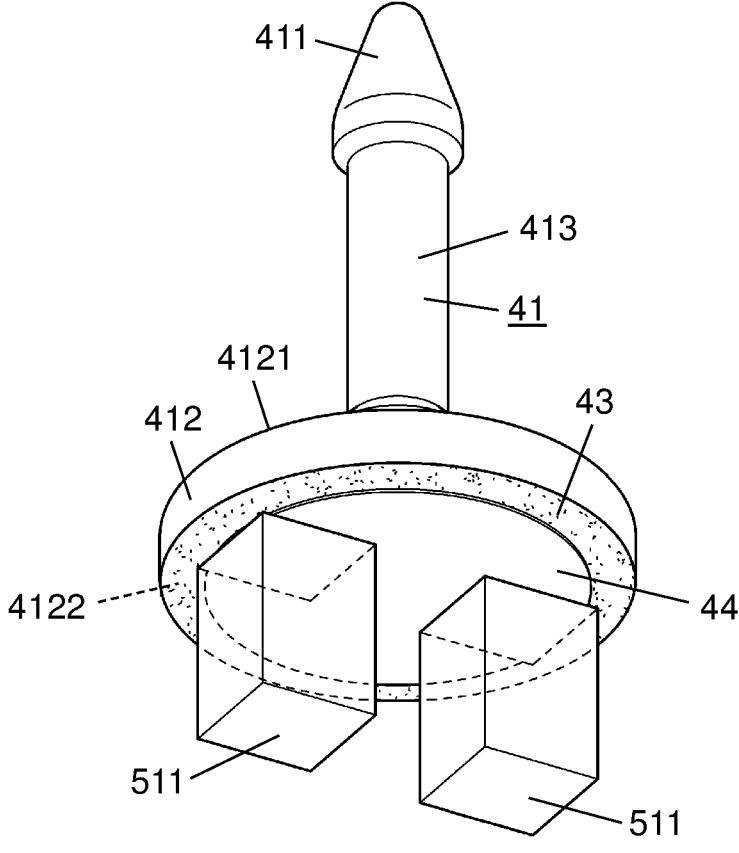
FIG. 4 is a perspective view of a discharge electrode included in the discharge device as viewed from below.

Furthermore, discharge device 10 according to the present exemplary embodiment further includes current limiting element 43. FIG. 4 is a perspective view of discharge electrode 41 included in discharge device 10 as viewed from below. Current limiting element 43 is electrically connected to a side of discharge electrode 41 opposite to counter electrode 42 side. Specifically, current limiting element 43 is electrically connected to base end part 412 provided at one end of discharge electrode 41 in a longitudinal direction. Current limiting element 43 has a function of limiting a current flowing through discharge electrode 41. Accordingly, it is possible to reduce discharge energy between discharge electrode 41 and counter electrode 42.

In discharge device 10 according to the present exemplary embodiment, radicals are generated by generating discharge between discharge electrode 41 and counter electrode 42. The radicals are the basis for providing useful effects in various situations, besides sterile filtration, odor removal, moisture keeping, freshness keeping, and inactivation of viruses. Here, ozone is also generated when radicals are generated by discharge. In the discharge generated between discharge electrode 41 and counter electrode 42, a relatively large current can instantaneously flow. Thus, the discharge energy between discharge electrode 41 and counter electrode 42 increases and a discharge space is greatly expanded. Accordingly, a reaction with oxygen in the atmosphere is promoted and the amount of generated ozone increases.

In discharge device 10 according to the present exemplary embodiment, as described above, the current (discharge current) flowing through discharge electrode 41 is limited by current limiting element 43. Accordingly, it possible to reduce the discharge energy between discharge electrode 41 and counter electrode 42, and as a result, since the discharge space is reduced, the reaction with oxygen in the atmosphere is suppressed, and the amount of generated ozone can be suppressed. On the other hand, since the discharge space of the discharge generated between discharge electrode 41 and counter electrode 42 is hardly widened and is generated near discharge electrode 41, radicals obtained by a reaction with water can be increased. That is, in accordance with discharge device 10 according to the present exemplary embodiment, it is possible to increase the amount of generated radicals while suppressing the amount of generated ozone, and it is possible to improve radical generation efficiency. Furthermore, since the discharge energy can be reduced, not only the amount of generated ozone but also the amount of generated $NO_X$ (for example, $NO_2$ that is a target substance of environmental standards in the Basic Environment Law) can be suppressed.

(2) DETAILS

Figure 2:
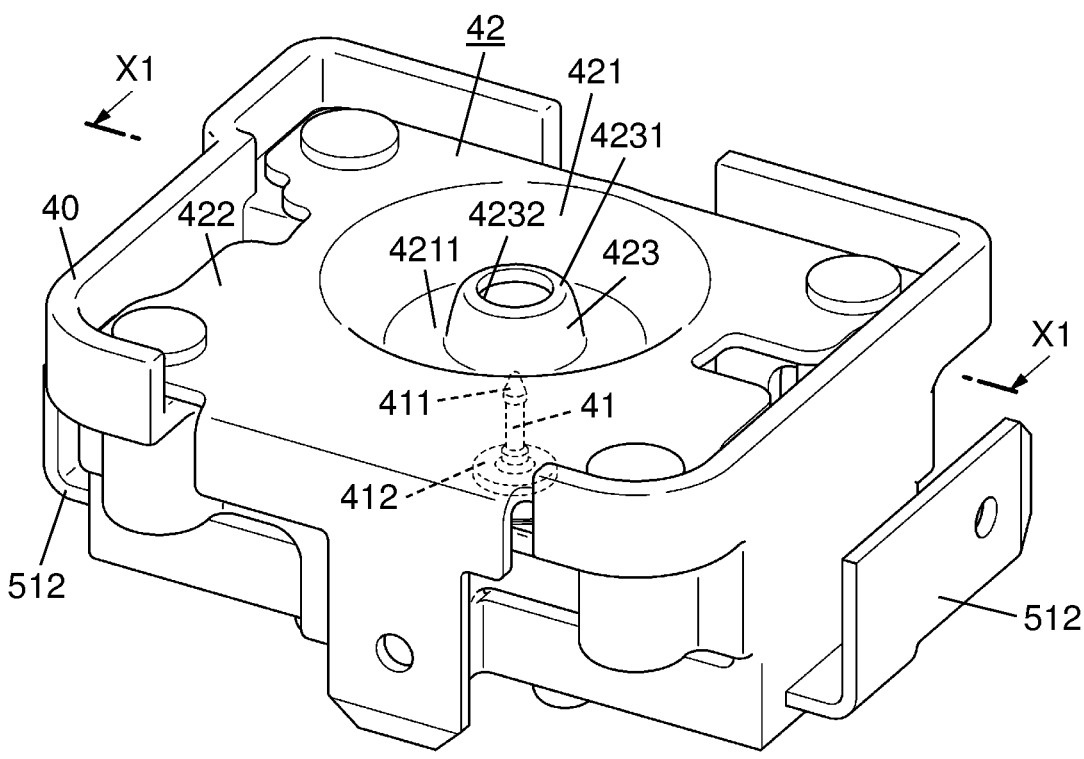
FIG. 2 is a perspective view of a load included in the discharge device.
Figure 3:
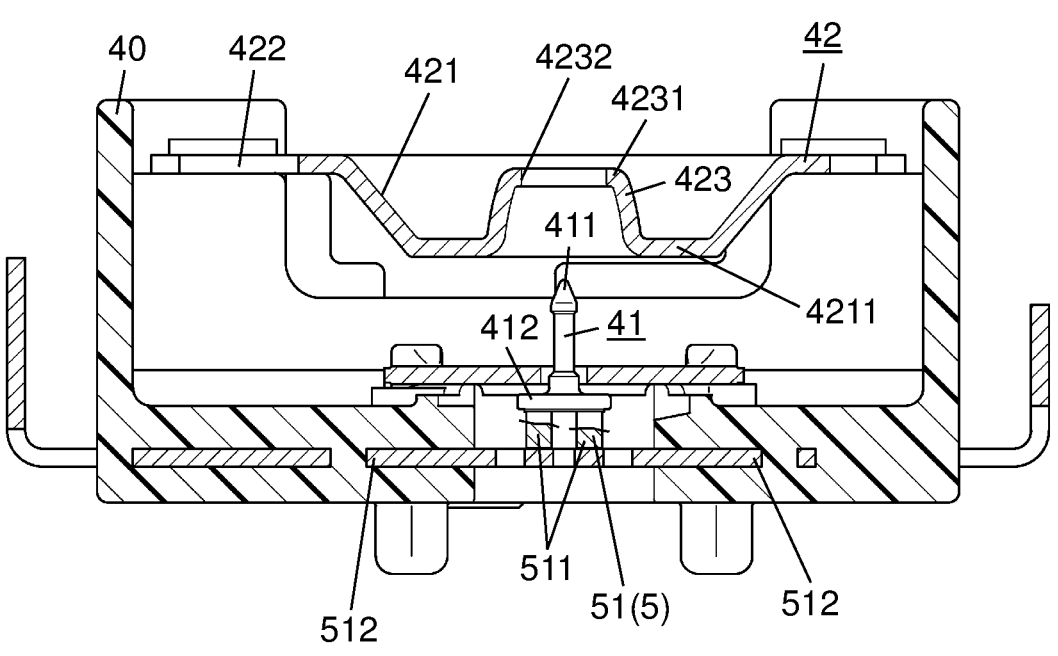
FIG. 3 is a cross-sectional view of the load taken along line X1-X1 in FIG. 2.
Figure 5:
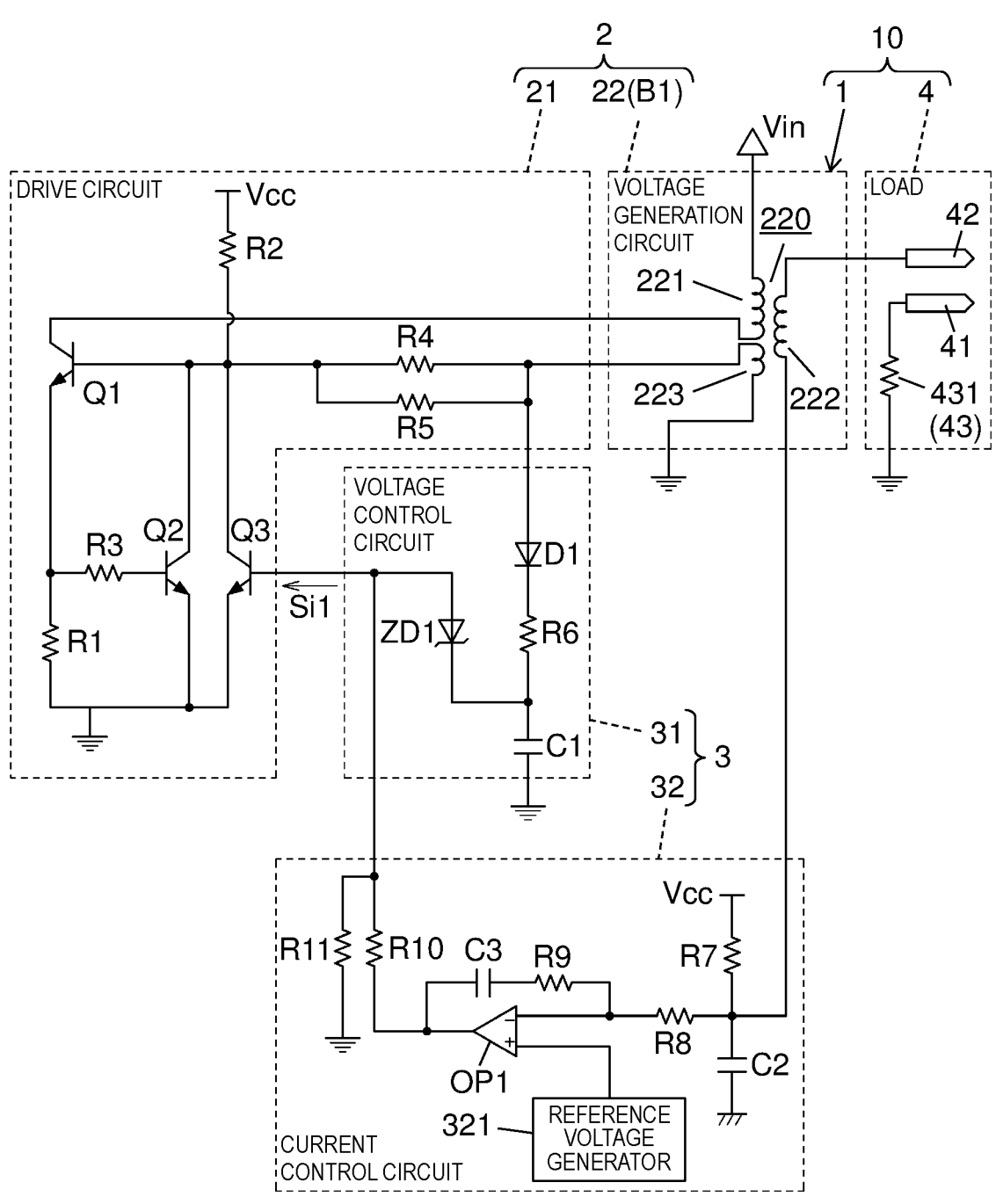
FIG. 5 is a circuit diagram illustrating an example of the discharge device.
Figure 6:
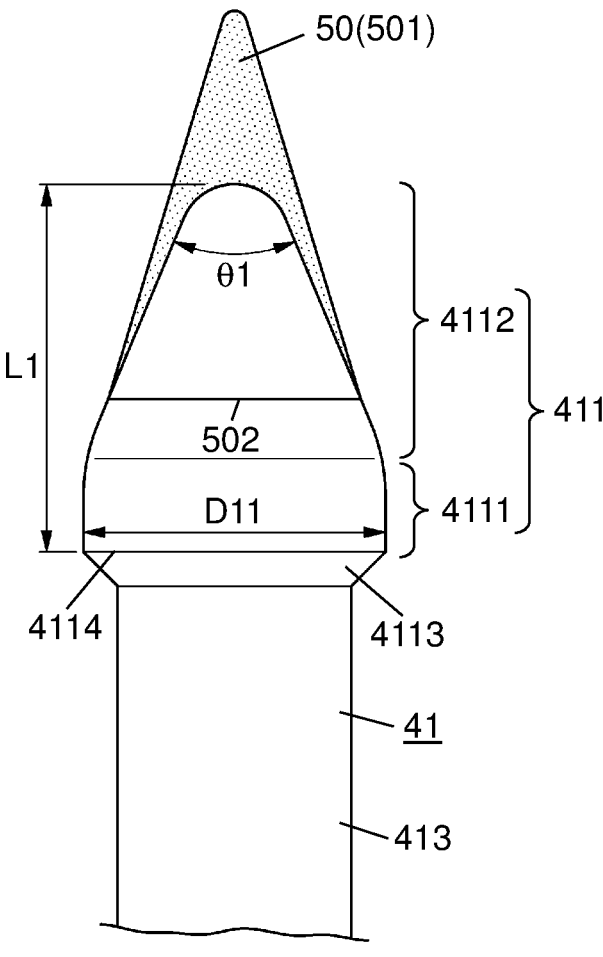
FIG. 6 is a schematic diagram illustrating a distal end shape of the discharge electrode.

Hereinafter, details of discharge device 10 according to the present exemplary embodiment will be described with reference to FIGS. 1 to 6. FIG. 2 is a perspective view of load 4 included in discharge device 10. FIG. 3 is a cross-sectional view of load 4 taken along line X1-X1 in FIG. 2. FIG. 4 is a perspective view of the discharge electrode included in the discharge device as viewed from below. FIG. 5 is a circuit diagram illustrating an example of discharge device 10. FIG. 6 is a schematic diagram illustrating a distal end shape of discharge electrode 41 included in discharge device 10.

(2.1) Overall Configuration

As illustrated in FIG. 1, discharge device 10 according to the present exemplary embodiment includes voltage application device 1, load 4, and liquid supply unit 5. Voltage application device 1 includes voltage application circuit 2 and control circuit 3. Load 4 includes discharge electrode 41 and counter electrode 42. Liquid supply unit 5 supplies liquid 50 to discharge electrode 41. In FIG. 1, shapes of discharge electrode 41 and counter electrode 42 are schematically illustrated.

Discharge electrode 41 is a rod-shaped electrode. As illustrated in FIGS. 2 and 3, discharge electrode 41 includes distal end part 411 at one end in the longitudinal direction, and includes base end part 412 at the other end (an end opposite to distal end part 411) in the longitudinal direction. Furthermore, as illustrated in FIG. 4, for example, discharge electrode 41 is formed integrally and continuously with base end part 412, and further includes shaft 413 extending toward distal end part 411. Distal end part 411 extends in one direction (longitudinal direction of discharge electrode 41) with respect to base end part 412. Discharge electrode 41 is a needle electrode in which distal at least distal end part 411 is formed in a tapered shape. The "tapered shape" as used herein is not limited to a shape in which the distal end is sharply pointed, and includes a shape in which the distal end is rounded as illustrated in FIG. 6. Note that the shape of distal end part 411 will be described in the section of "(2.3) Shape of distal end part".

Counter electrode 42 is disposed to face distal end part 411 of discharge electrode 41. Counter electrode 42 has, for example, a plate shape and has recess 421 at a central portion (see FIG. 3). Recess 421 is formed in a truncated cone shape by recessing a part of counter electrode 42 toward discharge electrode 41. Protrusion 423 is integrally formed at a central portion of bottom wall 4211 of recess 421. Protrusion 423 is formed in a truncated cone shape by protruding a part of bottom wall 4211 of recess 421 to a side opposite to discharge electrode 41 side. That is, a recessed direction of recess 421 (a direction in which recess 421 is recessed) is opposite to a protruding direction of protrusion 423. Opening portion 4232 is formed at a central portion of bottom wall 4231 of protrusion 423. Opening portion 4232 penetrates bottom wall 4231 in a thickness direction of bottom wall 4231. Here, a positional relationship between counter electrode 42 and discharge electrode 41 is determined such that a thickness direction of counter electrode 42 (a penetration direction of opening portion 4232) coincides with the longitudinal direction of discharge electrode 41 and distal end part 411 of discharge electrode 41 is positioned near a center of opening portion 4232 of counter electrode 42. That is, at least opening portion 4232 of protrusion 423 counter electrode 42 secures a gap (space) between counter electrode 42 and discharge electrode 41. In other words, discharge electrode 41 is disposed to face counter electrode 42 with a gap interposed therebetween, and is electrically insulated from counter electrode 42.

More specifically, for example, discharge electrode 41 and counter electrode 42 are formed in shapes illustrated in FIGS. 2 and 3. That is, counter electrode 42 includes support 422 and protrusion 423. Discharge electrode 41 and counter electrode 42 are held in housing 40 that has electric insulation and is made of synthetic resin. Support 422 has a flat plate shape, and recess 421 recessed in a truncated cone shape is formed on discharge electrode 41 side. Protrusion 423 protruding in a truncated cone shape on a side opposite to discharge electrode 41 side is integrally formed with bottom wall 4211 of recess 421. Opening portion 4232 opened in a circular shape is formed in bottom wall 4231 of protrusion 423. In this case, discharge is generated between an opening end edge of opening portion 4232 formed in bottom wall 4231 of protrusion 423 and distal end part 411 of discharge electrode 41.

As illustrated in FIG. 4, base end part 412 of discharge electrode 41 is formed in a disk shape. Base end part 412 has first surface 4121 and second surface 4122. First surface 4121 is a surface of base end part 412 on distal end part 411 side. As illustrated in FIG. 4, shaft 413 is formed in an elongated columnar shape, and a first end (a lower end in FIG. 4) thereof is disposed in a substantially central portion of first surface 4121. Furthermore, a second end (an upper end in FIG. 4) of shaft 413 on a side opposite to the first end is connected to distal end part 411 with throttle part 4113 (see FIG. 6) to be described later interposed therebetween. Second surface 4122 of base end part 412 is a surface opposite to distal end part 411 side. That is, first surface 4121 and second surface 4122 of base end part 412 face each other in the longitudinal direction (one direction) of discharge electrode 41. On second surface 4122 of base end part 412, current limiting element 43 is formed over entire second surface 4122. Here, in FIG. 4, dot hatching is applied to current limiting element 43 such that current limiting element 43 and conduction member 44 to be described later can be easily distinguished. Current limiting element 43 is directly and electrically connected to base end part 412 of discharge electrode 41 on the side opposite to counter electrode 42 side. More particularly, current limiting element 43 is directly and electrically connected to second surface 4122 of base end part 412. A shape of current limiting element 43 is a circular shape as viewed from the longitudinal direction of discharge electrode 41. Current limiting element 43 is, for example, an insulating film made of silicon carbide oxide (SiCO). Current limiting element 43 is formed by, for example, chemical vapor deposition (CVD) for second surface 4122 of base end part 412. Current limiting element 43 is, for example, a thin film having a thickness of 4 μm. In the present disclosure, the "thin film" refers to a thin film having a thickness of 10 μm or less. Current limiting element 43 includes resistance element 431 as illustrated in FIG. 5. That is, in the present exemplary embodiment, the insulating film is not a film that electrically insulates two elements (here, discharge electrode 41 and a pair of Peltier elements 511 illustrated in FIG. 4 and to be described later are used), but is a film having a function as resistance element 431 between two elements. A resistance value of current limiting element 43 is preferably, for example, from 1 MΩ to 900 MΩ inclusive. More preferably, the resistance value of current limiting element 43 is preferably more than or equal to 10 MΩ. The resistance value of current limiting element 43 is, for example, 300 MΩ. As described above, current limiting element 43 includes an insulating film having a function as resistance element 431. Furthermore, one Peltier element is connected to the ground and is connected to a high-voltage circuit.

conduction member 44 is formed on a surface of current limiting element 43 (a surface opposite to base end part 412 side of discharge electrode 41) (see FIG. 4). A shape of conduction member 44 is a circular shape having a diameter smaller than a diameter of current limiting element 43 as viewed from the longitudinal direction of discharge electrode 41. conduction member 44 is, for example, a thin film. conduction member 44 has a function of conducting a pair of Peltier elements 511 to be described later. In discharge device 10 according to the present exemplary embodiment, the pair of Peltier elements 511 are mechanically and electrically connected to conduction member 44 by, for example, soldering. Here, current limiting element 43 is a thin film, as described above. Therefore, even though current limiting element 43 is interposed between discharge electrode 41 and the pair of Peltier elements 511, cooling performance of discharge electrode 41 by the pair of Peltier elements 511 can be maintained.

Liquid supply unit 5 supplies liquid 50 for electrostatic atomization to discharge electrode 41. For example, liquid supply unit 5 is implemented by using cooling device 51 that cools discharge electrode 41 and generates dew condensation water from discharge electrode 41. Specifically, cooling device 51 includes, for example, a pair of Peltier elements 511 and a pair of radiator plates 512, as illustrated in FIG. 3. The pair of Peltier elements 511 are held by the pair of radiator plates 512. Cooling device 51 cools discharge electrode 41 by conducting the pair of Peltier elements 511. A part of each of the pair of radiator plates 512 is embedded in housing 40, and thus, the pair of radiator plates 512 are held by housing 40. At least a portion of the pair of radiator plates 512 holding Peltier element 511 is exposed from housing 40 (see FIG. 3).

As described above, the pair of Peltier elements 511 are mechanically and electrically connected to conduction member 44 by, for example, soldering. Therefore, the pair of Peltier elements 511 are in contact with discharge electrode 41 with current limiting element 43 interposed therebetween. Furthermore, the pair of Peltier elements 511 are mechanically and electrically connected to the pair of radiator plates 512 by, for example, soldering. The pair of Peltier elements 511 are conducted through the pair of radiator plates 512, conduction member 44, current limiting element 43, and discharge electrode 41. Therefore, cooling device 51 constituting liquid supply unit 5 cools entire discharge electrode 41 through base end part 412. Accordingly, moisture in the air condenses and adheres to the surface of discharge electrode 41 as dew condensation water. As a result, liquid 50 is retained in discharge electrode 41. That is, liquid supply unit 5 is configured to cool discharge electrode 41, and generate dew condensation water as liquid 50 on the surface of discharge electrode 41. In this configuration, since liquid supply unit 5 can supply liquid 50 (dew condensation water) to discharge electrode 41 by using moisture in the air, supply and replenishment of the liquid to discharge device 10 become unnecessary.

As illustrated in FIG. 1, voltage application circuit 2 includes drive circuit 21 and voltage generation circuit 22 functioning as step-up circuit B1. Drive circuit 21 is a circuit that drives voltage generation circuit 22. Voltage generation circuit 22 is a circuit that receives power supply from input unit 6 and generates a voltage to be applied to load 4 (an applied voltage). Input unit 6 is a power supply circuit that generates a DC voltage of approximately several V to a dozen of V. In the present exemplary embodiment, it is assumed that input unit 6 is not included in the components of voltage application device 1. However, input unit 6 may be included in the components of voltage application device 1. Specific circuit configurations of drive circuit 21 and voltage generation circuit 22 (step-up circuit B1) will be described in the section of "(2.2) Circuit configuration".

Voltage application circuit 2 is electrically connected to load 4 (discharge electrode 41 and counter electrode 42) (see FIG. 5). Voltage application circuit 2 applies a high voltage to load 4. Here, voltage application circuit 2 is configured to apply a high voltage between discharge electrode 41 and counter electrode 42 while designating discharge electrode 41 as a negative electrode (ground) and counter electrode 42 as a positive electrode (plus). In other words, in a state where a high voltage is applied from voltage application circuit 2 to load 4, a potential difference with counter electrode 42 side as a high potential and discharge electrode 41 side as a low potential is produced between discharge electrode 41 and counter electrode 42. The "high voltage" as used herein may be any voltage set to cause discharge in discharge electrode 41, such as a voltage having a peak of approximately 7.0 kV. However, the high voltage applied from voltage application circuit 2 to load 4 is not limited to about 7.0 kV, and is appropriately set in accordance with, for example, the shapes of discharge electrode 41 and counter electrode 42 and a distance between discharge electrode 41 and counter electrode 42.

Here, an actuation mode of voltage application circuit 2 includes two modes of a first mode and a second mode. The first mode is a mode of increasing an applied voltage with the lapse of time, causing discharge to develop into dielectric breakdown, and generating a discharge current. The second mode is a mode for cutting off the discharge current by control circuit 3 or the like in order to terminate the discharge. That is, voltage application circuit 2 has, as the actuation modes, the first mode and the second mode. The first mode is a mode for increasing the applied voltage with the lapse of time to generate the discharge current. The second mode is a mode for cutting off the discharge current.

Control circuit 3 controls voltage application circuit 2. Control circuit 3 controls voltage application circuit 2 such that voltage application circuit 2 alternately repeats the first mode and the second mode during a drive period for driving voltage application device 1. Here, control circuit 3 switches between the first mode and the second mode at a drive frequency such that the magnitude of the applied voltage applied from voltage application circuit 2 to load 4 (transformer voltage to be described below) periodically varies by the drive frequency.

Accordingly, the magnitude of an electric energy acting on liquid 50 retained in discharge electrode 41 periodically varies by the drive frequency, and as a result, liquid 50 retained in discharge electrode 41 mechanically vibrates by the drive frequency. Here, voltage generation circuit 22 (step-up circuit B1) varies the magnitude of the applied voltage such that a frequency (drive frequency) of the variation of the applied voltage is more than or equal to a resonance frequency (natural frequency) of liquid 50 retained in discharge electrode 41. Note that, as the drive frequency is set to a value near the resonance frequency of liquid 50, an amplitude of the mechanical vibration of liquid 50 caused by the variation of the magnitude of the applied voltage becomes relatively large.

In the present exemplary embodiment, control circuit 3 controls voltage application circuit 2 based on a monitored target. The "monitored target" as used herein includes at least one of an output current or an output voltage of voltage application circuit 2.

Here, control circuit 3 includes voltage control circuit 31 and current control circuit 32 as illustrated in FIGS. 1 and 5. Voltage control circuit 31 controls drive circuit 21 of voltage application circuit 2 based on the monitored target including the output voltage of voltage application circuit 2. Control circuit 3 outputs control signal Si1 to drive circuit 21, and controls drive circuit 21 by control signal Si1. Current control circuit 32 controls drive circuit 21 of voltage application circuit 2 based on the monitored target including the output current of voltage application circuit 2. That is, in the present exemplary embodiment, control circuit 3 controls voltage application circuit 2 by using both the output current and the output voltage of voltage application circuit 2 as the monitored targets. However, there is a correlation between the output voltage (secondary side voltage) of voltage application circuit 2 and a primary side voltage of voltage application circuit 2. Accordingly, voltage control circuit 31 may indirectly detect the output voltage of voltage application circuit 2 from the primary side voltage of voltage application circuit 2. Similarly, there is a correlation between the output current (secondary side current) of voltage application circuit 2 and an input current (primary side current) of voltage application circuit 2. Accordingly, current control circuit 32 may indirectly detect the output current of voltage application circuit 2 from the input current of voltage application circuit 2. Specific circuit configurations of voltage control circuit 31 and current control circuit 32 will be described in the section of "(2.2) Circuit configuration".

Control circuit 3 is configured to operate voltage application circuit 2 in the first mode when the magnitude of the monitored target is less than a threshold value, and operate voltage application circuit 2 in the second mode when the magnitude of the monitored target is more than or equal to the threshold value. That is, voltage application circuit 2 operates in the first mode until the magnitude of the monitored target reaches the threshold value, and the applied voltage increases with the lapse of time. At this time, in discharge electrode 41, corona discharge starts due to dielectric breakdown, and a discharge current is generated. When the magnitude of the monitored target reaches the threshold value, voltage application circuit 2 operates in the second mode, and the applied voltage decreases. At this time, the potential difference between discharge electrode 41 and counter electrode 42 is lost, and the discharge current is cut off by control circuit 3 and the like. In other words, control circuit 3 or the like detects the discharge of load 4 via voltage application circuit 2, and decreases the applied voltage to extinguish the discharge current (into disappearance).

Accordingly, during the drive period, voltage application circuit 2 operates to alternately repeat the first mode and second mode, and the magnitude of the applied voltage periodically varies by the drive frequency. As a result, in discharge electrode 41, the discharge is intermittently repeated.

More specifically, discharge device 10 first generates local corona discharge by liquid 50 retained in distal end part 411 of discharge electrode 41, but turns to the second mode immediately after the start of discharge, and discharge is intermittently generated between discharge electrode 41 and counter electrode 42.

Figure 7A:
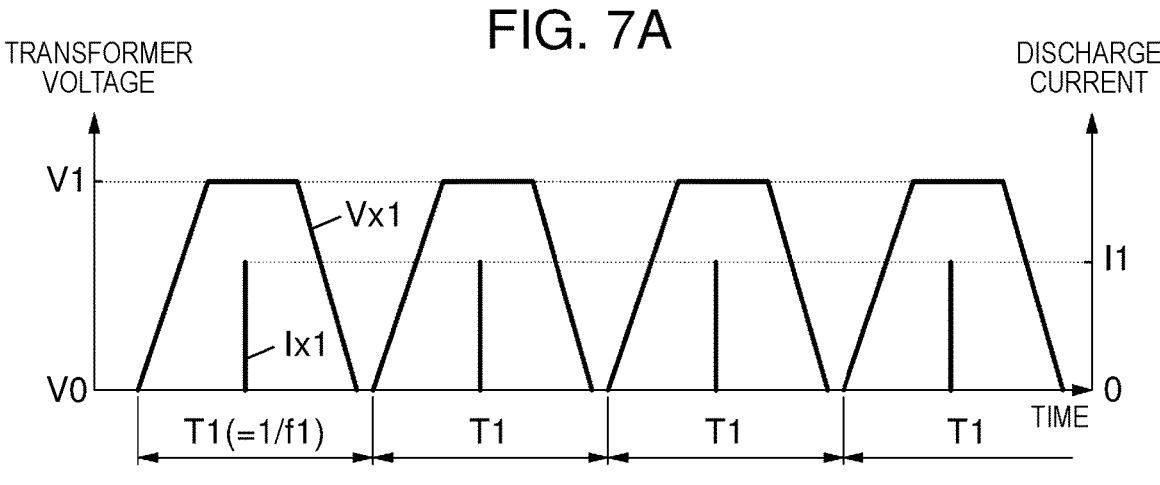
FIG. 7A is a graph schematically showing a discharge form of the discharge device.
Figure 7B:
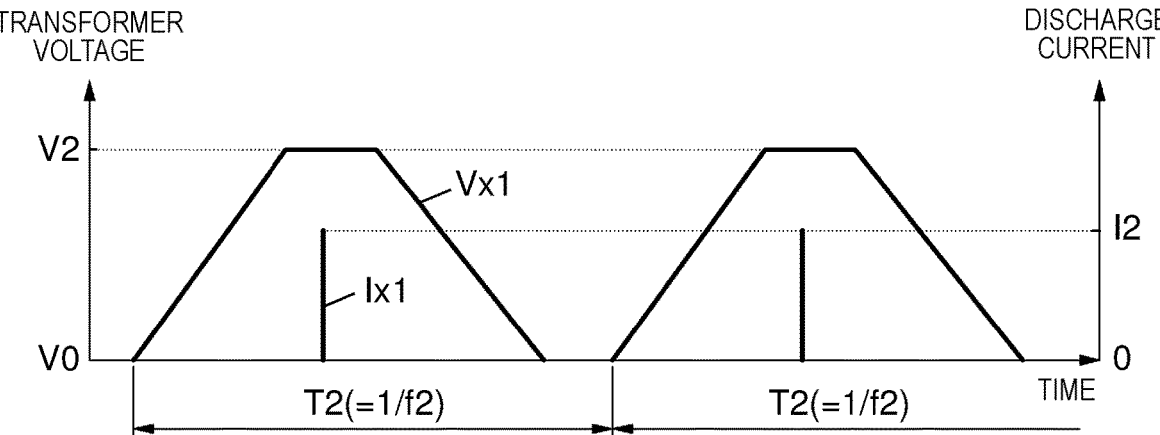
FIG. 7B is a graph schematically showing a discharge form of a discharge device according to a comparative example.

FIG. 7A is a graph showing a discharge form (voltage waveform Vx1 and current waveform Ix1) of discharge device 10 according to the present exemplary embodiment. In FIG. 7A, a horizontal axis represents a time axis, a left vertical axis represents the output voltage (applied voltage, that is, transformer voltage) of voltage application circuit 2, and a right vertical axis represents the discharge current. The applied voltage increases, and dielectric breakdown occurs at a distal end of liquid 50, and minute discharge is generated due to corona discharge. When the applied voltage is maximum value V1, discharge is formed, and then the voltage is rapidly decreased to stop the discharge. Note that FIG. 7B is a graph showing a discharge form of a discharge device of a comparative example, and details thereof will be described later.

As illustrated in FIG. 7A, the magnitude of the applied voltage (transformer voltage) periodically varies in discharge cycles T1, and when the drive frequency is set to "f1", discharge cycle T1 is expressed by a reciprocal (1/f1) of drive frequency f1. Note that, in the present exemplary embodiment, for example, the magnitude of the applied voltage (transformer voltage) varies in a range exceeding 0 V during the drive period. Here, minimum value V0 of the applied voltage is more than 0 V, and the magnitude of the applied voltage varies between minimum value V0 and maximum value V1. The applied voltage increases substantially linearly and decreases substantially linearly with the lapse of time in each discharge cycle T1.

In each discharge cycle T1, control circuit 3 operates voltage application circuit 2 in the first mode until the magnitude of the monitored target is less than the threshold value, that is, the applied voltage reaches the threshold value (for example, maximum value V1 in FIG. 7A) and the output current reaches the threshold value (for example, threshold value I1 in FIG. 7A). In each discharge cycle T1, control circuit 3 operates voltage application circuit 2 in the second mode when the magnitude of the monitored target becomes more than or equal to the threshold value, that is, when the output current becomes more than or equal to the threshold value.

Incidentally, as described above, drive frequency f1 is set to be more than or equal to resonance frequency fr1 (a natural frequency) of liquid 50 retained in discharge electrode 41. Resonance frequency fr1 of liquid 50 depends on, for example, a volume (amount) of liquid 50 and is expressed by $fr1 = a \times V^{-0.5}$. "V" is a volume of liquid 50 retained discharge electrode 41. "$\alpha$" is a coefficient of proportionality depending on a surface tension, a viscosity, and the like of liquid 50 retained in discharge electrode 41.

Therefore, resonance frequency fr1 of liquid 50 is increased by reducing the volume of liquid 50 retained in discharge electrode 41.

Discharge device 10 according to the present exemplary embodiment applies a voltage from voltage application circuit 2 to load 4 in a state where liquid 50 (dew condensation water) is supplied (held) to discharge electrode 41. Accordingly, in load 4, discharge is generated between discharge electrode 41 and counter electrode 42 due to the potential difference between discharge electrode 41 and counter electrode 42. At this time, liquid 50 retained in discharge electrode 41 is electrostatically atomized by the discharge. As a result, discharge device 10 produces a nanometer-sized charged fine particle liquid containing radicals. That is, discharge device 10 constitutes a so-called charged fine particle liquid generation device. The produced charged fine particle liquid is released to a periphery of discharge device 10 via, for example, opening portion 4232 of counter electrode 42.

(2.2) Circuit Configuration

Next, a specific circuit configuration of voltage application device 1 is described with reference to FIG. 5. FIG. 5 is a circuit diagram schematically illustrating an example of a circuit configuration of discharge device 10. Note that the illustration of input unit 6 is omitted in FIG. 5.

Voltage application circuit 2 includes drive circuit 21 and voltage generation circuit 22 as described above. In the example of FIG. 5, voltage application circuit 2 is an isolated DC/DC converter. Voltage application circuit 2 includes step-up circuit B1 that steps up input voltage Vin (for example, 13.8 V) from input unit 6 and outputs the stepped-up voltage as the output voltage. Here, voltage generation circuit 22 functions as step-up circuit B1. The output voltage of step-up circuit B1 is applied to load 4 (discharge electrode 41 and counter electrode 42) as the applied voltage. That is, voltage application circuit 2 generates discharge in discharge electrode 41 by applying the voltage to load 4.

Voltage generation circuit 22 (step-up circuit B1) includes isolation transformer 220 (step-up transformer) including primary winding 221, secondary winding 222, and auxiliary winding 223. Primary winding 221 and auxiliary winding 223 are electrically insulated from secondary winding 222, and are magnetically coupled. One end of secondary winding 222 is electrically connected to counter electrode 42. That is, step-up circuit B1 includes a step-up transformer (isolation transformer 220) that steps up input voltage Vin input to a primary side (primary winding 221 side) and applies an output voltage from a secondary side (secondary winding 222 side) electrically connected to load 4.

Here, step-up circuit B1 is configured to be able to periodically vary the output voltage at a frequency more than or equal to the resonance frequency of liquid 50. In particular, in the present exemplary embodiment, a value of an inductance on the secondary side (secondary winding 222 side) of the step-up transformer (isolation transformer 220) is set to the magnitude that enables the output voltage to vary at the frequency more than equal to the resonance frequency of liquid 50.

The "inductance on the secondary side" as used herein is an effective inductance on the secondary side (secondary winding 222 side), and is obtained by multiplying self-inductance L on secondary winding 222 side by coupling coefficient k (0 and 1). The value of the inductance on the secondary side can be set by adjusting a permeability of a core, the number of windings of secondary winding 222, a length, a cross-sectional area, and the like.

In the present exemplary embodiment, the value of the inductance on the secondary side of the step-up transformer (isolation transformer 220) is less than or equal to 900 mH. Specifically, the value of the inductance on the secondary side is more than or equal to 50 mH as a lower limit value and is less than or equal to 900 mH. The value of the inductance on the secondary side is preferably less than or equal to 500 mH, and more preferably less than or equal to 100 mH.

The value of the inductance is set in this manner, and thus, even though the resonance frequency of liquid 50 is relatively high (for example, more than or equal to 1.5 kHz), step-up circuit B1 can vary the output voltage at a drive frequency more than or equal to the resonance frequency to follow the resonance frequency.

Drive circuit 21 includes transistor Q1, and is configured to supply a power to primary winding 221 of isolation transformer 220 by a switching operation of transistor Q1. Drive circuit 21 includes transistor Q2, transistor Q3, and resistors R1 to R5 in addition to transistor Q1. Transistors Q1, Q2, and Q3 are, for example, npn bipolar transistors.

A collector of transistor Q1 is connected to primary winding 221, and an emitter of transistor Q1 is connected to the ground with resistor R1 interposed therebetween. Input voltage Vin is applied to a series circuit of primary winding 221, transistor Q1, and resistor R1 from input unit 6. A base of transistor Q1 is connected to control power supply Vcc with resistor R2 interposed therebetween. Control power supply Vcc applies a control voltage (for example, 5.1 V) to drive circuit 21.

Collectors of transistors Q2 and Q3 are connected to the base of transistor Q1. Emitters of transistors Q2 and Q3 are connected to the ground. A base of transistor Q2 is connected to the emitter of transistor Q1 with resistor R3 interposed therebetween. The base of transistor Q1 is connected to one end of auxiliary winding 223 with a parallel circuit of resistors R4 and R5 interposed therebetween. Another end of auxiliary winding 223 is connected to the ground. A base of transistor Q3 is connected to control circuit 3 (voltage control circuit 31 and current control circuit 32) to input control signal Si1 from control circuit 3.

With the above configuration, voltage application circuit 2 constitutes a self-excited converter. That is, when transistor Q1 is turned on and a current flows to primary winding 221 of isolation transformer 220, a voltage across resistor R1 increases, and transistor Q2 is turned on. Accordingly, since the base of transistor Q1 is connected to the ground with transistor Q2 interposed therebetween, transistor Q1 is turned off. When transistor Q1 is turned off, the current flowing through primary winding 221 is cut off, the voltage across resistor R1 decreases, and transistor Q2 is turned off. Accordingly, a high voltage is induced to secondary winding 222 of isolation transformer 220, and is applied to load 4 as the output voltage of voltage application circuit 2. At this time, a voltage is also induced to auxiliary winding 223 due to an induced voltage generated in secondary winding 222, a voltage between the base and the emitter of transistor Q1 increases, and transistor Q1 is turned on. Voltage application circuit 2 steps up input voltage Vin by repeating the above operation, and applies the output voltage to load 4.

As illustrated in FIG. 5, control circuit 3 includes voltage control circuit 31 and current control circuit 32.

Voltage control circuit 31 includes diode D1, resistor R6, capacitor C1, and Zener diode ZD1. An anode of diode D1 is connected to connecting points between auxiliary winding 223 and resistors R4 and R5. A cathode of diode D1 is connected to one end of capacitor C1 with resistor R6 interposed therebetween. Another end of capacitor C1 is connected to the ground. Further, a cathode of Zener diode ZD1 is connected to one end of capacitor C1 (a connecting point with resistor R6). An anode of Zener diode ZD1 is connected to the base of transistor Q3 as an output terminal of voltage control circuit 31.

With the above configuration, voltage control circuit 31 indirectly monitors the output voltage of voltage application circuit 2 (the induced voltage of secondary winding 222) as the monitored target by monitoring an induced voltage of auxiliary winding 223. That is, while the output voltage of voltage application circuit 2 is less than the threshold value (maximum value V1), Zener diode ZD1 of voltage control circuit 31 is turned off. On the other hand, when the output voltage of voltage application circuit 2 becomes greater than or equal to the threshold value (maximum value V1), Zener diode ZD1 of voltage control circuit 31 is turned on. At this time, control signal Si1 exceeds a control threshold value, a voltage is applied between the base and the emitter of transistor Q3, and transistor Q3 is turned on. Accordingly, since a base current of transistor Q1 flows to the ground with transistor Q3 interposed therebetween, a collector current of transistor Q1 decreases. Accordingly, when the output voltage of voltage application circuit 2 is equal to or higher than the threshold value (maximum value V1), voltage control circuit 31 decreases the switching energy of drive circuit 21 of voltage application circuit 2.

Current control circuit 32 includes operational amplifier OP1, reference voltage generator 321, resistors R7 to R11, and capacitors C2 and C3. One end of capacitor C2 is connected to control power supply Vcc via resistor R7. Another end of capacitor C2 is connected to the ground. Control power supply Vcc applies a control voltage (for example, 5.1 V) to a series circuit of resistor R7 and capacitor C2. A connecting point of resistor R7 and capacitor C2 (the one end of capacitor C2) is connected to an inverted input terminal of operational amplifier OP1 via resistor R8. Furthermore, an end part (the other end) on an opposite side to counter electrode 42 of secondary winding 222 of isolation transformer 220 is connected to the connecting point (the one end of capacitor C2) of resister R7 and capacitor C2. In other words, control power supply Vcc is connected to counter electrode 42 with resistor R7 and secondary winding 222 interposed therebetween. A non-inverted input terminal of operational amplifier OP1 is connected to reference voltage generator 321, and a reference voltage is input to the non-inverted input terminal from reference voltage generator 321. A series circuit of resistor R9 and capacitor C3 is connected between the inverted input terminal and an output terminal of operational amplifier OP1. The output terminal of operational amplifier OP1 is connected to one end of resistor R10. Another end of resistor R10 is connected to the ground via resistor R11. A connecting point of resister R10 and resister R11 (the other end of resister R10) is connected to the base of transistor Q3 as an output terminal of current control circuit 32.

With the above configuration, current control circuit 32 monitors an induced current at secondary winding 222, thereby monitoring the output current (induced voltage at secondary winding 222) of voltage application circuit 2 that is the monitored target. Stated another way, while the output current of voltage application circuit 2 is less than a threshold value, an output of operational amplifier OP1 of current control circuit 32 has a low level (L-level). If the output current of voltage application circuit 2 becomes greater than or equal to the threshold value, the output of operational amplifier OP1 of current control circuit 32 has a high level (H-level). At this time, control signal Si1 exceeds a control threshold value, a voltage is applied between the base and the emitter of transistor Q3, and transistor Q3 is turned on. Accordingly, since a base current of transistor Q1 flows to the ground with transistor Q3 interposed therebetween, a collector current of transistor Q1 decreases. Accordingly, when the output current of voltage application circuit 2 is greater than or equal to the threshold value, current control circuit 32 reduces energy to be input from drive circuit 21 of voltage application circuit 2 to voltage generation circuit 22.

(2.3) Shape of Distal End Part

Next, the shape of distal end part 411 of discharge electrode 41 will be described with reference to FIG. 6. In FIG. 6, dot hatching is applied to Taylor cone 501 such that distal end part 411 and Taylor cone 501 formed at distal end part 411 can be easily distinguished.

As illustrated in FIG. 6, the shape of distal end part 411 of discharge electrode 41 is, for example, a shape including a conical portion. A shape of a portion of distal end part 411 facing counter electrode 42 (here, a shape of a distal end of the conical portion) is, for example, an R shape. That is, a shape of a portion of distal end part 411 on a side opposite to base end part 412 side is an R shape.

Distal end part 411 includes first portion 4111 and second portion 4112. First portion 4111 is a portion of distal end part 411 closer to base end part 412 than second portion 4112, and has a columnar shape. Second portion 4112 is a portion of distal end part 411 farther from base end part 412 than first portion 4111, and has a conical shape. In short, distal end part 411 has first portion 4111 corresponding to a cylindrical portion and second portion 4112 corresponding to a conical portion.

First portion 4111 and second portion 4112 are arranged in the order of first portion 4111 and second portion 4112 from base end part 412 side in the longitudinal direction of discharge electrode 41. Note that a shape of second portion 4112 is preferably a substantially conical shape as illustrated in FIG. 6, but is not limited thereto. The shape of second portion 4112 may be a curved surface shape protruding toward counter electrode 42, specifically, may be a hemispherical shape, a bell shape, or the like. Furthermore, distal end part 411 of the present exemplary embodiment has a shape obtained by combining second portion 4112 (conical portion) and first portion 4111 (cylindrical portion) having a different shape from the second portion. Distal end part 411 may include only a portion (for example, a conical portion) having a single shape as a whole, for example, by omitting first portion 4111.

In the present exemplary embodiment, for example, throttle part 4113 is provided between distal end part 411 and shaft 413. That is, distal end part 411 and shaft 413 are connected with throttle part 4113 interposed therebetween. Throttle part 4113 is formed in a tapered shape in which a diameter decreases from end edge 4114 of distal end part 411 toward shaft 413. Throttle part 4113 is provided, and thus, it is possible to prevent excessive dew condensation water generated on shaft 413 side from joining dew condensation water (Taylor cone) on distal end part 411 side. Note that, in order to obtain the same effect of suppressing joining, instead of throttle part 4113, a protruding portion having a larger diameter to protrude in a radial direction than both distal end part 411 and shaft 413 may be provided between distal end part 411 and shaft 413. Furthermore, in place of tapered throttle part 4113, a stepped portion may be provided between distal end part 411 and shaft 413.

The maximum diameter of distal end part 411 including the conical portion is equal to maximum diameter D11 of first portion 4111 (hereinafter, a maximum diameter of distal end part 411 is also referred to as "maximum diameter D11"). Maximum diameter D11 of distal end part 411 is preferably, for example, from 0.35 mm to 1.5 mm inclusive. Maximum diameter D11 of distal end part 411 is, for example, 0.710 mm. Apex angle θ1 of second portion 4112 is, for example, 47.580°. Furthermore, total length L1 of distal end part 411 (a length dimension of distal end part 411 in the longitudinal direction of discharge electrode 41) is, for example, 0.830 mm. Here, for example, total length L1 of distal end part 411 is a length from end edge 4114 on base end part 412 side to a distal end of second portion 4112 in a substantially cylindrical portion having maximum diameter D11 of first portion 4111 as a diameter as illustrated in FIG. 6. Note that, in a case where first portion 4111 is omitted, total length L1 of distal end part 411 is a length of second portion 4112.

Here, in a case where maximum diameter D11 of distal end part 411 is 1.5 mm, a ratio of total length L1 of distal end part 411 to maximum diameter D11 of distal end part 411 is 1.6. Furthermore, in a case where maximum diameter D11 of distal end part 411 is 0.35 mm, the ratio of total length L1 of distal end part 411 to maximum diameter D11 of distal end part 411 is 1.0. That is, in discharge device 10 according to the present exemplary embodiment, a ratio of total length L1 of distal end part 411 in one direction (the longitudinal direction of discharge electrode 41) to maximum diameter D11 of distal end part 411 (hereinafter, also referred to as a "first ratio") is from 1.0 to 1.6 inclusive. In other words, total length L1 of distal end part 411 in one direction is a length more than or equal to maximum diameter D11 of distal end part 411. For example, in a case where maximum diameter D11 of distal end part 411 is 0.710 mm and total length L1 of distal end part 411 is 0.830 mm, the first ratio is 1.169. As described above, when the first ratio is from 1.0 to 1.6 inclusive, the volume of liquid 50 forming Taylor cone 501 can be reduced, and as a result, the resonance frequency of liquid 50 can be increased. Accordingly, it possible to reduce the discharge energy between discharge electrode 41 and counter electrode 42, and as a result, since the discharge space is reduced, the reaction with oxygen in the atmosphere is suppressed, and the amount of generated ozone can be suppressed. On the other hand, the discharge generated between discharge electrode 41 and counter electrode 42 is generated by a radio frequency, and thus, the discharge space due to the discharge between discharge electrode 41 and counter electrode 42 is hardly widened. As a result, the discharge space is generated near discharge electrode 41, and thus, the radicals obtained by the reaction with water can be increased. That is, in accordance with discharge device 10 according to the present exemplary embodiment, it is possible to increase the amount of generated radicals while suppressing the amount of generated ozone, and it is possible to improve radical generation efficiency.

Incidentally, a voltage is applied between discharge electrode 41 and counter electrode 42, and thus, Taylor cone 501 is formed at distal end part 411 of discharge electrode 41 by liquid 50 retained in discharge electrode 41. As illustrated in FIG. 6, the shape of Taylor cone 501 is a conical shape along the conical portion of distal end part 411 of discharge electrode 41. Second portion 4112 of distal end part 411 of discharge electrode 41 enters Taylor cone 501. That is, in discharge device 10 according to the present exemplary embodiment, second portion 4112 constitutes a part of distal end part 411 entering Taylor cone 501.

Furthermore, as described above, in order to increase the resonance frequency of liquid 50 forming Taylor cone 501, a ratio of a volume of second portion 4112 of distal end part 411 of discharge electrode 41 to a volume of Taylor cone 501 (hereinafter, also referred to as a "second ratio") is preferably from 0.6 to 0.95 inclusive. For example, in a case where the volume of Taylor cone 501 is 0.0917 mm³ and the volume of second portion 4112 is 0.0650 mm³, the second ratio is 0.71. For example, in the case of not having the above shape, the volume of liquid 50 forming Taylor cone 501 is 0.23 μL, and at this time, the resonance frequency of liquid 50 is 1 kHz. On the other hand, in the shape of the present exemplary embodiment having the above shape, the volume of liquid 50 forming Taylor cone 501 is 0.076 μL, and at this time, the resonance frequency of liquid 50 is 3 kHz. As described above, the resonance frequency of liquid 50 can be increased by reducing the volume of liquid 50 forming Taylor cone 501.

In discharge device 10 according to the present exemplary embodiment, as described above, second portion 4112 of distal end part 411 of discharge electrode 41 enters Taylor cone 501. In this case, outer peripheral edge 502 of Taylor cone 501 is preferably positioned between a first position and a second position. Outer peripheral edge 502 of Taylor cone 501 is a portion of Taylor cone 501 farthest from counter electrode 42 in a direction in which discharge electrode 41 and counter electrode 42 are arranged. In the example of FIG. 6, a shape of outer peripheral edge 502 of Taylor cone 501 is an annular shape as viewed from the longitudinal direction of discharge electrode 41. The first position is a position where a distance from a distal end of distal end part 411 is 0.62 times total length L1 of distal end part 411. The second position is a position where a distance from the distal end of distal end part 411 is 1.00 times total length L1 of distal end part 411. For example, as described above, in a case where total length L1 of distal end part 411 is 0.830 mm, outer peripheral edge 502 of Taylor cone 501 is positioned between a position (first position) where the distance from the distal end of distal end part 411 is 0.515 mm and a position (second position) where the distance is 0.830 mm.

(2.4) Improvement of Number of Times of Discharge

Hereinafter, improvement of the number of times of discharge in discharge device according to the present exemplary embodiment will be described with reference to FIGS. 7A and 7B.

As described above, the applied voltage to load 4, that is, the magnitude of the output voltage (transformer voltage) is varied by the drive frequency (discharge frequency), and thus, the magnitude of the electric energy acting on liquid 50 retained in discharge electrode 41 periodically varies by the drive frequency. As a result, liquid 50 mechanically vibrates by the drive frequency. When the drive frequency is set to be more than or equal to the resonance frequency of liquid 50, the amplitude of the mechanical vibration of liquid 50 caused by the variation of the magnitude of the applied voltage becomes relatively large. As the amplitude of liquid 50 increases, the distal end part of Taylor cone 501 (see FIG. 6) has a pointed (sharper) shape, and discharging is facilitated.

Incidentally, in discharge device 10, the voltage is decreased in the second mode after the start of discharge, and thus, it is possible to stop continuous discharge caused by the corona discharge. Accordingly, it is possible to stop the continuous discharge in which ozone is likely to be generated. It is possible to generate a large amount of radicals while suppressing an increase in ozone by repeating this discharge at a high speed, that is, by increasing the drive frequency.

As described above, the resonance frequency of liquid 50 depends on the volume of liquid 50 retained in discharge electrode 41. The shape of distal end part 411 of discharge electrode 41 is set as described above, and thus, the volume of liquid 50 retained in discharge electrode 41 is reduced to increase the resonance frequency of liquid 50. Assuming that the resonance frequency of the liquid retained in the discharge electrode not having the above shape is, for example, 1 kHz, the resonance frequency of liquid 50 retained in discharge electrode 41 having the above shape is more than or equal to 1.5 kHz (for example, 3 kHz). The drive frequency is increased to be more than or equal to 1.5 kHz (for example, when the resonance frequency is 3 kHz, 3 kHz to 5 kHz.) following the resonance frequency increased to be more than or equal to 1.5 kHz, and as a result, the amplitude of the mechanical vibration of liquid 50 increases, and discharge efficiency is improved.

On the other hand, in order to increase the drive frequency to follow the resonance frequency increased to be more than or equal to 1.5 kHz, it is necessary to quickly step up the transformer voltage in the first mode to the threshold value (maximum value V1). Furthermore, when the continuous discharge caused by the corona discharge described above continues, there is a possibility that a new atomization discharge cannot be formed, and it is necessary to generate next atomization discharge after stopping the continuous discharge. In order to stop the continuous discharge, it is necessary to decrease the transformer voltage or alleviate the sharpness of Taylor cone 501 formed by the transformer voltage, and it is necessary to increase a speed of decreasing the transformer voltage.

Therefore, in the present exemplary embodiment, the value of the inductance on the secondary side of the step-up transformer (isolation transformer 220) is set to be less than or equal to 900 mH in order to increase a speed of increasing and decreasing the transformer voltage.

FIG. 7B is a graph showing a discharge form (voltage waveform Vx1 and current waveform Ix1) of the discharge device of the comparative example. Similarly to FIG. 7A, in FIG. 7B, a horizontal axis represents a time axis, a left vertical axis represents the output voltage (applied voltage, that is, transformer voltage) of the voltage application circuit, and a right vertical axis represents the discharge current. Maximum value V2 (threshold value) of the transformer voltage illustrated in FIG. 7B is assumed to be the same as maximum value V1 (threshold value) of the transformer voltage illustrated in FIG. 7A, but may be different from maximum value V1. Furthermore, threshold value I2 of the discharge current illustrated in FIG. 7B is assumed to be the same as threshold value I1 of the discharge current illustrated in FIG. 7A, but may be different from threshold value I1. It is assumed that time scales of the horizontal axes in FIGS. 7A and 7B are the same.

In the discharge device of the comparative example, the value of the inductance on the secondary side of the step-up transformer is set to, for example, 3000 mH, but the shape of distal end part 411 of discharge electrode 41 described above is adopted, and the resonance frequency of liquid 50 is increased. Originally, the drive frequency is desirably increased following the increased resonance frequency, but in the comparative example in which the value of the inductance is set to 3000 mH, a time for stepping up to maximum value V2 is slow, a time for stepping down to minimum value V0 is also slow, and drive frequency f2 is about 1 kHz. As a result, discharge cycle T2 in the comparative example is longer than discharge cycle T1.

On the other hand, in discharge device 10 of the present exemplary embodiment set to be less than or equal to 900 mH, a time for stepping up to maximum value V1 is faster and a time for stepping down to minimum value V0 is also faster than in the discharge device of the comparative example. In the illustrated example, discharge cycle T1 is substantially half of discharge cycle T2. That is, the number of times of discharge of discharge device 10 within a predetermined period is approximately twice the number of times of discharge of the discharge device of the comparative example.

As described above, the step-up transformer (isolation transformer 220) of the present exemplary embodiment in which the value of the inductance on the secondary side is set to be less than or equal to 900 mH is configured to be able to periodically vary the output voltage by a frequency more than or equal to the resonance frequency of liquid 50. Thus, the number of times of discharge of discharge device 10 is increased, and as a result, it is possible to improve radical generation efficiency.

In particular, in discharge device 10, although discharge energy by one discharge is smaller than the discharge energy of the discharge device of the comparative example by shortening discharge cycle T1, the amount of generated radicals is improved and the amount of generated ozone is suppressed by increasing the number of times of discharge. Furthermore, the discharge energy is suppressed by one discharge, and thus, the amount of generated $NO_2$ that increases depending on the increase in the discharge energy can also be suppressed.

(2.5) Operation

In the circuit configuration illustrated in FIG. 5, control circuit 3 performs an operation to be described below, and thus, discharge device 10 generates discharge with suppressed energy between discharge electrode 41 and counter electrode 42.

That is, during a period before dielectric breakdown occurs, control circuit 3 uses the output voltage of voltage application circuit 2 as the monitored target. when the output voltage as the monitored target becomes more than or equal to the threshold value (for example, maximum value V1 in FIG. 7A), voltage control circuit 31 reduces switching energy of drive circuit 21. On the other hand, after the occurrence of the dielectric breakdown, control circuit 3 uses the output current of the voltage application circuit 2 as the monitored target, and when the output current as the monitored target becomes more than or equal to the threshold value (for example, threshold value I1 in FIG. 7A), current control circuit 32 stops a switching operation of drive circuit 21. Accordingly, voltage application circuit 2 operates in the second mode in which the transformer voltage is decreased to cut off the discharge current by causing load 4 to be in an overload state against voltage application circuit 2. That is, the actuation mode of voltage application circuit 2 is switched from the first mode to the second mode.

At this time, both the output voltage and the output current of voltage application circuit 2 decrease, and therefore control circuit 3 restarts a switching operation of drive circuit 21. Accordingly, voltage application circuit 2 operates in the first mode in which discharge occurs by increasing the applied voltage with the lapse of time. That is, the actuation mode of voltage application circuit 2 is switched from the first mode to the second mode.

Control circuit 3 repeats the above-described operation, and therefore voltage application circuit 2 operates to alternately repeat the first mode and the second mode. As a result, discharge electrode 41 is switched between ON and OFF of the discharge. Voltage application circuit 2 of the present exemplary embodiment can vary the output voltage by the drive frequency more than or equal to the resonance frequency of liquid 50.

(3) MODIFICATIONS

The above-described exemplary embodiment is merely one of various exemplary embodiments of the present disclosure. The above-described exemplary embodiment can be variously changed in accordance with design and the like as long as the object of the present disclosure can be achieved. Hereinafter, modifications of the above-described exemplary embodiment will be listed. The modifications to be described below can be applied in appropriate combination.

(3.1) First Modification

Figure 8:
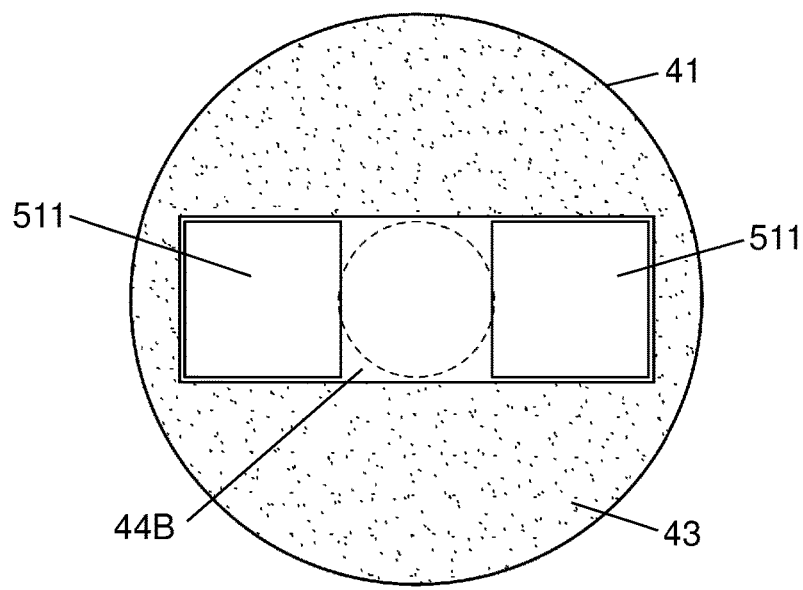
FIG. 8 is a bottom view of a discharge electrode included in a discharge device according to a first modification of the exemplary embodiment.

FIG. 8 is a bottom view of discharge electrode 41 included in the discharge device according to a first modification. In the above-described exemplary embodiment, the shape of conduction member 44 that conducts the pair of Peltier elements 511 is a circular shape as viewed from the longitudinal direction of discharge electrode 41. However, the present disclosure is not limited thereto, and for example, as in conduction member 44B illustrated in FIG. 8, the conduction member may have a rectangular shape as viewed from the longitudinal direction of discharge electrode 41. In this case, a width dimension (dimension in an up-down direction in FIG. 8) of conduction member 44B is preferably the same as a width dimension (dimension in the up-down direction in FIG. 8) of each Peltier element 511, but may be more than the width dimension of each Peltier element 511. In this case, conduction member 44B is also preferably a thin film. Further, the shape of the conduction member may be, for example, an elliptical shape as viewed from the longitudinal direction of discharge electrode 41. That is, the conduction member may have any shape as long as the conduction member can conduct the pair of Peltier elements 511.

(3.2) Second Modification

In the above-described exemplary embodiment, an upper limit value of maximum diameter D11 of distal end part 411 of discharge electrode 41 is 0.71 mm, but the present disclosure is not limited thereto. The upper limit value of maximum diameter D11 of distal end part 411 of discharge electrode 41 may be, for example, 0.600 mm. That is, maximum diameter D11 of distal end part 411 of discharge electrode 41 may be, for example, less than or equal to 0.600 mm. Furthermore, maximum diameter D11 of distal end part 411 of discharge electrode 41 is preferably, for example, more than or equal to 0.500 mm. In this case, the volume of liquid 50 forming Taylor cone 501 can be further reduced, and as a result, the resonance frequency of liquid 50 can be further increased. Accordingly, it possible to further reduce discharge energy between discharge electrode 41 and counter electrode 42. As a result, since the discharge space is further reduced, the reaction with oxygen in the atmosphere is suppressed, and the amount of generated ozone can be further suppressed. On the other hand, the radicals obtained by the reaction with water can be further increased by further generating the discharge generated between discharge electrode 41 and counter electrode 42 by the radio frequency. That is, in accordance with discharge device 10 according to the present exemplary embodiment, it is possible to further increase the amount of generated radicals while further suppressing the amount of generated ozone, and it is possible to further improve the radical generation efficiency. In this case, maximum diameter D11 of distal end part 411 of discharge electrode 41 is more preferably less than or equal to 0.550 mm. That is, maximum diameter D11 of distal end part 411 of discharge electrode 41 is more preferably from 0.500 mm to 0.550 mm inclusive.

(3.3) Other Modifications

Liquid supply unit 5 is not limited to the configuration in which discharge electrode 41 is cooled to generate dew condensation water on discharge electrode 41. Liquid supply unit 5 may be configured to supply liquid 50 from a tank to discharge electrode 41 by using a capillary phenomenon or a supply mechanism such as a pump, for example. Further, liquid 50 is not limited to water (including dew condensation water), and may be a liquid other than water.

FIG. 5 is merely an example of a circuit configuration of discharge device 10, and a specific circuit configuration of voltage application device 1 can be appropriately changed. For example, voltage application circuit 2 is not limited to a self-excited converter, but may be a separately excited converter. Furthermore, in voltage application circuit 2, transistors Q1, Q2, and Q3 are not limited to bipolar transistors, and may be, for example, metal-oxide-semiconductor field effect transistors (MOSFETs). Further, voltage generation circuit 22 may be implemented by a transformer (a voltage transformer) including a piezoelectric element.

Current limiting element 43 is not limited to resistance element 431, and may include a capacitance element. That is, current limiting element 43 may include at least one of resistance element 431 or a capacitance element.

Current limiting element 43 is not limited to an insulating film made of silicon carbide oxide, and may be, for example, an oxide film (NiO) of nickel (Ni). In this case, in current limiting element 43, for example, an oxide film of nickel is formed by applying a nickel paste to second surface 4122 of base end part 412 of discharge electrode 41 and then sintering the applied nickel paste. Furthermore, current limiting element 43 may be, for example, an insulating film made of diamond-like carbon (DLC). Further, current limiting element 43 may be an insulating film made of, for example, aluminum nitride (AlN). Furthermore, current limiting element 43 may be, for example, an oxide film (TiO) of titanium (Ti). Furthermore, current limiting element 43 may be made of, for example, a sintered material having high thermal conductivity. Furthermore, current limiting element 43 may be, for example, a binder product in which two sheets of copper (Cu) are bonded by using an epoxy resin (EP) as a binder, or a binder product in which two sheets of copper are bonded by using aluminum oxide ($AlO_3$ or $Al_2O_3$) as a binder.

Furthermore, in a comparison between two values such as the monitored target and the threshold value, the phrase "more than or equal to" includes both a case where two values are equal to each other and a case where one of two values exceeds another. However, the present disclosure is not limited to this definition, and "more than or equal to" as used herein may be synonymous with "more than" including only a case where one of two values exceeds the other. That is, whether the case of two values equal to each other is included may be changed in any manner depending on settings of threshold values and the like. Accordingly, which of "more than or equal to" and "more than" is used does not produce a technical difference. Similarly, "less than" may be synonymous with "less than or equal to".

A needle-shaped projection may be provided on counter electrode 42, and leader discharge that develops from corona discharge to strong discharge to intermittently generate dielectric breakdown (breakdown of the entire path) may be used. In this case, a plurality of needle-shaped parts may be disposed at equal intervals in a circumferential direction of opening portion 4232. Each needle-shaped part may protrude from an inner peripheral edge of opening portion 4232 toward a center of opening portion 4232. Each needle-shaped part may obliquely protrude from the inner peripheral edge of opening portion 4232 such that a distance to discharge electrode 41 in a longitudinal direction of discharge electrode 41 becomes shorter toward a distal end part of each of the needle-shaped portions. Each needle-shaped part is formed in the shape described above, and thus, electric field concentration easily occurs in a distal end part of each needle-shaped part. As a result, discharge is easily and stably generated between the distal end part of each needle-shaped part and distal end part 411 of discharge electrode 41.

ASPECTS

The following aspects are disclosed based on the above-described exemplary embodiment, modifications, and the like.

Discharge device (10) according to a first aspect includes discharge electrode (41), voltage application circuit (2), and current limiting element (43). Discharge electrode (41) is disposed to face counter electrode (42). Voltage application circuit (2) is electrically connected to discharge electrode (41) and counter electrode (42) with discharge electrode (41) as a ground side. Voltage application circuit (2) generates discharge between discharge electrode (41) and counter electrode (42) by applying a voltage between discharge electrode (41) and counter electrode (42). Current limiting element (43) is electrically connected to a side of discharge electrode (41) opposite to counter electrode (42). Current limiting element (43) limits a current flowing to discharge electrode (41).

In accordance with this aspect, it is possible to improve radical generation efficiency.

In discharge device (10) according to a second aspect, in the first aspect, current limiting element (43) includes at least one of resistance element (431) or a capacitance element.

In accordance with this aspect, it is possible to improve radical generation efficiency.

Discharge device (10) according to a third aspect further includes liquid supply unit (5) in the first or second aspect. Liquid supply unit (5) supplies liquid (50) for electrostatic atomization to discharge electrode (41). Liquid supply unit (5) includes Peltier element (511). Peltier element (511) is thermally coupled to discharge electrode (41) with current limiting element (43) interposed therebetween.

In accordance with this aspect, it is possible to supply liquid (50) to discharge electrode (41) by liquid supply unit (5) while improving radical generation efficiency.

In discharge device (10) according to a fourth aspect, in the third aspect, current limiting element (43) is a thin film.

In accordance with this aspect, it is possible to supply liquid (50) to discharge electrode (41) by liquid supply unit (5) while improving radical generation efficiency by current limiting element (43).

In discharge device (10) according to a fifth aspect, in any one of the first to fourth aspects, a resistance value by current limiting element (43) is more than or equal to 1 M$\Omega$.

In accordance with this aspect, it is possible to improve radical generation efficiency.

Discharge device (10) according to a sixth aspect further includes counter electrode (42) in any one of the first to fifth aspects.

In accordance with this aspect, it is possible to improve radical generation efficiency by discharge generated between discharge electrode (41) and counter electrode (42).

In discharge device (10) according to a seventh aspect, in any one of the first to sixth aspects, liquid (50) retained in discharge electrode (41) is electrostatically atomized by the discharge.

In accordance with this aspect, it is possible to generate charged fine particle water containing radicals while improving radical generation efficiency.

The configurations according to the second to seventh aspects are not essential to discharge device (10), and can be omitted as appropriate.

REFERENCE SIGNS LIST

2 voltage application circuit
5 liquid supply unit
10 discharge device
41 discharge electrode
42 counter electrode
43 current limiting element
431 resistance element
50 liquid
511 Peltier element

The invention claimed is:

1. A discharge device comprising:
a discharge electrode that is disposed to face a counter electrode, the discharge electrode retaining a liquid;
a voltage application circuit that is electrically connected to the discharge electrode and the counter electrode with the discharge electrode as a ground side, the voltage application circuit generating discharge between the discharge electrode and the counter electrode by applying a voltage between the discharge electrode and the counter electrode;
a current limiting element that is electrically connected to a side of the discharge electrode opposite to the counter electrode; and
a liquid supply unit that supplies a liquid for electrostatic atomization to the discharge electrode,
wherein the liquid supply unit includes a Peltier element thermally coupled to the discharge electrode, and the current limiting element is interposed between the Peltier element and the discharge electrode.

2. The discharge device according to claim 1, wherein the current limiting element includes at least one of a resistance element or a capacitance element.

3. The discharge device according to claim 1, wherein the current limiting element is a thin film.

4. The discharge device according to any one of claim 1, 2 or 3, wherein a resistance value by the current limiting element is more than or equal to 1 M$\Omega$.

5. The discharge device according to any one of claim 1, 2 or 3, further comprising the counter element electrode.

6. The discharge device according to any one of claim 1, 2 or 3, wherein the liquid retained in the discharge electrode is electrostatically atomized by the discharge.

7. The discharge device according to any one of claim 1, 2 or 3, wherein the current limiting element is electrically connected between the side of the discharge electrode opposite to the counter electrode and the ground.

8. The discharge device according to claim 2, wherein the current limiting element is a thin film.

9. The discharge device according to claim 8, wherein a resistance value by the current limiting element is more than or equal to 1 M$\Omega$.

10. The discharge device according to claim 8, further comprising the counter electrode.

11. The discharge device according to claim 8, wherein the liquid retained in the discharge electrode is electrostatically atomized by the discharge.

12. The discharge device according to claim 8, wherein the current limiting element is electrically connected between the side of the discharge electrode opposite to the counter electrode and the ground.

* * * * *